United States Patent [19]

Finley et al.

[11] 4,443,384

[45] Apr. 17, 1984

[54] PROCESS FOR THE MANUFACTURE OF MIXED PHOSPHORIC ACID ESTER COMPOSITIONS

[75] Inventors: Joseph H. Finley, Metuchen; Hsiang P. Liao, Princeton, both of N.J.

[73] Assignee: FMC Corporation, Philadelphia, Pa.

[21] Appl. No.: 432,471

[22] Filed: Oct. 4, 1982

[51] Int. Cl.$^3$ ............................................. C07F 9/09
[52] U.S. Cl. ........................................................ 260/982
[58] Field of Search ............................... 260/982, 965

[56] References Cited

U.S. PATENT DOCUMENTS

| | | | |
|---|---|---|---|
| T903,016 | 10/1972 | Cleveland | 260/982 |
| 2,504,121 | 4/1950 | Gamrath | 260/461 |
| 2,557,090 | 6/1951 | Gamrath et al. | 260/30.6 |
| 2,557,091 | 6/1951 | Gamrath et al. | 260/30.6 |
| 3,056,823 | 10/1962 | Hechenbleikner et al. | 260/461 |
| 3,184,496 | 5/1965 | Baranauckas et al. | 260/461 |
| 3,363,033 | 1/1968 | Witt | 260/982 |
| 3,553,155 | 1/1971 | Garrett | 260/30.6 |
| 3,576,923 | 4/1971 | Randell et al. | 260/966 |

FOREIGN PATENT DOCUMENTS 25720  3/1981  European Pat. Off. ............ 260/982

OTHER PUBLICATIONS

W. H. C. Rueggeberg et al. in J. Am. Chem. Soc. 70, 1802, (1948).
Chemical Abstracts, Abstract of Polish Pat. No. 78616.

*Primary Examiner*—Anton H. Sutto
*Attorney, Agent, or Firm*—Robert D. Jackson; Eugene G. Horsky; Eugene G. Seems

[57] ABSTRACT

Mixed phosphoric acid ester compositions containing less than 4 weight percent of a triaryl phosphate, from about 10 to about 20 weight percent of an aryl dialkyl phosphate and from about 65 to about 80 weight percent of an alkyl diaryl phosphate are prepared by heating a monohydric alcohol with aqueous sodium hydroxide to form the sodium alkoxide, distilling off the water as an alcohol azeotrope and reacting the alcohol sodium alkoxide with a triphenyl phenol. The mixed phosphoric acid ester composition may be separated from by-products of the reaction by distillation.

4 Claims, No Drawings

PROCESS FOR THE MANUFACTURE OF MIXED PHOSPHORIC ACID ESTER COMPOSITIONS

This invention relates to a new method of manufacture of known mixed esters of phosphoric acid by transesterification in the presence of a strong base. More particularly, this invention relates to an improved commercial process for the production of mixed phosphoric acid ester compositions containing less than about 4 weight percent of triphenyl phosphate having the formula:

$$(R_1O)_3P{=}O$$

from about 10 to about 20 weight percent of a phenyl dialkyl phosphate having the formula:

$$R_1O-\overset{\overset{\text{O}}{\|}}{P}-(OCH_2CH_2R_2)_2$$

and from about 65 to about 80 weight percent of an alkyl diphenyl phosphate having the formula:

$$(R_1O)_2-\overset{\overset{\text{O}}{\|}}{P}-OCH_2CH_2R_2$$

wherein $R_1$ is a phenyl radical and $R_2$ is an alkyl radical.

The mixed phosphoric acid ester compositions described in this application are characterized by high autogenous ignition temperatures, low pour points and compatibility with paraffinic hydrocarbon oils. They may be used, either alone or in combination with paraffinic hydrocarbon oils, to prepare hydraulic and torque converter fluids that have excellent stability at very high temperatures. Such mixed phosphoric acid ester compositions also find use as lubricants either alone or in combination with other known lubricants with which they are compatible. Combinations of such mixed phosphoric acid ester compositions with the alkanoic acid esters of organic polyhydroxy compound such as pentaerythritol, polymethylol ethane, trimethylol propane, neopentyl glycol and the like form heat stable high pressure lubricants.

Various methods are known for the production of mixed phosphoric acid ester compositions. However, few of the processes described in the art have proven to be commercially feasible. Millions of pounds of mixed aryl esters of phosphoric acid have been made by the process taught in U.S. Pat. No. 3,576,923 wherein phenol is alkylated in the presence of a Friedel-Crafts catalyst and the whole of the product resulting from the alkylation of the phenol is treated with phosphorus oxychloride. The resulting product is a mixed phosphate ester wherein the substituents on the phosphorus atoms are phenols and substituted phenols (generally $C_3$–$C_4$ substituted phenols). The process of the present invention may give a much more complex ester mixture than the composition taught in U.S. Pat. No. 3,576,923 in that the ester mixture may contain different ester species wherein the substituents on the phosphorus atom are derived from aliphatic alcohols, and alkoxyalcohols containing up to 18 carbon atoms in addition to phenols and substituted phenols.

The manufacture of alkyl diaryl phosphate esters is also known but the process employed to obtain such products is directed to esters of high purity containing a single species. A common procedure described is that of reacting 2 moles of phenol or similar hydroxyaryl compound with 1 mole of phosphorus oxychloride, removing the HCl formed under vacuum, and then reacting the diphenyl phosphoryl chloride with 1 mole of an aliphatic alcohol. This procedure is objectionable as the initial phosphorylation reaction is difficult to control and excessive quantitites of the triaryl derivatives are formed, necessitating distillation of a highly corrosive mixture of phosphoryl chlorides.

Another procedure for preparing an alkyl diaryl phosphate ester referred to in the prior art is that of preparing the triaryl phosphates, removing one aryl group by alkaline hydrolysis followed by steam distillation and then introducing the alkyl group. The principal objectionable feature of this process is that it is exceedingly costly in view of the increased number of steps required to produce the finished product.

Alkyl diaryl phosphates may also be prepared by reacting in excess of 1 mole of an aliphatic alcohol with 1 mole of phosphorus oxychloride, removing the HCl formed under vacuum, purifying the monoalkyl phosphoryl dichloride by distillation and subsequently reacting at a relatively high temperature the purified acid chloride with 2 moles of phenol or similar hydroxyaryl compound. According to this process, in order to obtain pure neutral phosphate esters, it is essential that the intermediate alkyl phosphoryl dichloride be separated from the reaction mixture and purified. This is accomplished by fractional distillation of the acid chloride from the reaction mass. Pure esters may also be obtained by fractionating the crude neutral phosphate esters. This process has given satisfactory results when the aliphatic alcohol used was a primary alcohol of relatively short chain length. However, it is known that secondary, tertiary, and substituted alcohols are not suited to this reaction. Typical alcohols which do not satisfactorily undergo the reaction described in this paragraph are the allyl or substituted allyl alcohols, nitro alcohols, secondary butyl alcohol, benzyl alcohol and 2-octanol.

Moreover, it has been found that the intermediate monoalkyl phosphoryl dichlorides which result when phosphate esters are manufactured by this method tend to decompose with such decomposition being dependent upon time and temperature. In the case of the lower alkyl phosphoryl dichlorides, such as the $C_1$–$C_4$ alkyl phosphoryl dichlorides, the boiling points of the compositions are lower than their respective decomposition temperature range under commercially practical subatmospheric pressure thereby permitting purification of the monoalkyl phosphoryl dichloride by fractionation. However, the decomposition temperature ranges of the higher molecular weight monoalkyl phosphoryl dichlorides which are intermediate to the formation of the monoalkyl diaryl phosphate esters that may be present in the mixed ester composition prepared by this process are lower than their respective boiling points that could be obtained under commercially feasible subatmospheric pressures, thus rendering purification of the intermediate monoalkyl phosphoryl dichlorides by commercial fractionation impossible. Furthermore, if purified intermediate alkyl phosphoryl dichlorides are obtained and subsequently reacted with hydroxyaryl compounds to form monoalkyl diaryl phosphates, the relatively high temperatures required to cause the reaction to proceed essentially quantitatively are again higher than the decomposition temperature ranges of the respective alkyl phosphoryl dichlorides and consequently decomposition again results.

A process for the manufacture of monoalkyl diaryl phosphate ester wherein the single alkyl group may contain from 6 to 18 carbon atoms and may be a beta-alkoxy-ethyl radical of 4 to 18 carbon atoms is described in U.S. Pat. Nos. 2,504,121 and 2,557,090 (alkyl group may contain 4–12 carbon atoms). Both patents, however, are directed to the preparation of pure monoalkyl diaryl phosphate esters. This process involves reaction of phosphorus oxychloride with one mole of an alcohol to yield a monophosphoryl dichloride, which is then reacted with two moles of a sodium phenate. This yields a product of high purity which is not as effective a plasticizer as the complex mixture of products that result from the present invention. Further, this method produces large quantities of sodium salts which are difficult to remove and dispose of. In addition, the side reaction of alkyl phosphoryl dichloride with alcohol produces substantial quantities of alkyl halide as a by-product.

The recently issued (1975) Polish Pat. No. 78,616 describes the transesterification of a triaryl phosphate with an aliphatic alcohol containing 6 to 12 carbon atoms in its molecule in the presence of 0.25–12 parts of sodium or potassium by weight at a temperature of 20° C.–200° C. for 1–10 hours, wherein the weight ratio of triaryl phosphate to alcohol may vary between 100:40 and 100:200. One technical advantage claimed in the Polish patent is that this process yields a final product of greater purity. The sole example of this patent, however, gives an impure residue that is dark yellow to brown in color which decomposes when attempts are made to purify it by vacuum distillation.

The transesterification of tertiary alkyl phosphates by heating with alcohols having a higher molecular weight radical than that present in the ester is also known. In the presence of a stoichiometric amount of sodium alkoxide, the reaction results in mixtures of mono- and di-exchange products in rather poor yields. Substantial quantities of ether are formed with the alkoxide and are present in the reaction mixture.

The use of sodium alkoxide catalysts in the transesterification of esters is described in the Journal of the American Chemical Society, 70, 1802 (1948).

Mixed phosphoric acid ester compositions containing phenyl and substituted phenyl groups attached to the phosphorus atom through an oxygen linkage are known and are described in U.S. Pat. No. 3,576,923 (referred to above) and U.S. Pat. No. 3,553,155. Alkoxy diaryl phosphates are also known and are described in U.S. Pat. Nos. 2,557,090 and 2,557,091. The patents referred to above mention that certain phosphate esters are useful as plasticizers for polyvinyl chloride polymers.

U.S. patent application Ser. No. 160,786, filed June 18, 1980 (now pending) describes and claims a mixed phosphoric acid ester composition containing no more than about 4 weight percent of triaryl phosphate, from about 10 to about 20 weight percent of an aryl dialkyl phosphate having the formula:

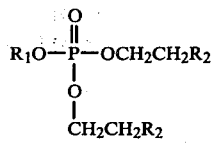

and 65 to 80 weight percent of an alkyl diaryl phosphate having the formula:

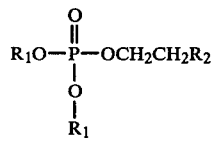

wherein $R_1$ is the same or a different aromatic radical selected from the group consisting of phenyl and substituted phenyl radicals and $R_2$ is the same or a different aliphatic radical selected from the group consisting of alkyl and alkoxy radicals.

This pending United States patent application also discloses and claims a method of making such mixed phosphoric acid ester compositions by reacting in an anhydrous system and in the presence of a catalytic amount of sodium, a phosphoric acid ester

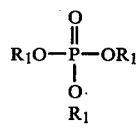

wherein $R_1$ may be the same or a different aromatic radical selected from the group consisting of phenyl and substituted phenyl radicals, with an aliphatic alcohol having the formula:

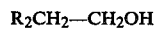

$R_2CH_2-CH_2OH$ wherein $R_2$ is the same or a different aliphatic radical selected from the group consisting of alkyl and alkoxy radicals. This application teaches that the mixed phosphoric acid ester composition so obtained may be separated as a colorless liquid from impurities present in the transesterification mixture by vacuum distillation.

U.S. patent application Ser. No. 160,786, filed June 16, 1980 teaches that maintaining anhydrous conditions throughout the reaction is critical in effecting the transesterification reaction by the process therein described. That application teaches, that, " . . . as many of the alcohols employed, and particularly the lower molecular weight alcohols are hydroscopic, precautions must be taken that all reactants are thoroughly dry. The presence of moisture has a pronounced effect on the transesterification of esters of phosphoric acid and modifies the composition of the reaction product to an extent that does not occur in the alcoholysis of esters derived from organic acids." Furthermore, the process described and claimed in that application was catalyzed by small amounts of metallic sodium, as it was found that sodium alkoxide, that was prepared externally of the reaction and then added to the reaction mixture in catalytic amounts, was much less effective.

In view of the teachings of the prior art, one would not believe that commercial production of mixed phosphoric acid ester compositions containing less than about 4 weight percent of triphenyl phosphate having the formula:

$$(R_1O)_3P=O$$

from about 10 to about 20 weight percent of an aryl dialkyl phosphate having the formula:

$$R_1O-\overset{\overset{O}{\|}}{P}-(OCH_2CH_2R_2)_2$$

and from about 65 to about 80 weight percent of an alkyl diaryl phosphate having the formula:

$$(R_1O)_2-\overset{\overset{O}{\|}}{P}-OCH_2CH_2R_2$$

wherein $R_1$ is a phenyl radical, and $R_2$ is an alkyl radical might be effected utilizing an aqueous solution of a strong base as the catalyst.

First, considering the prior art teaching that moisture adversely effected the transesterification reaction, it would not be expected that the addition of an aqueous solution of a strong base might be substituted for metallic sodium. Secondly, the prior art leads away from the present invention in that sodium alkoxide was indicated to be an inefficient catalyst for the desired reaction. In addition, an unexpected advantage is obtained by the process of the present invention since the composition of the mixed phosphoric ester that is obtained, and particularly the amount of triaryl phosphate that is present in that composition may be controlled by the amount of aqueous base that is added to the transesterification mixture. The substitution of sodium hydroxide for metallic sodium avoids the hazard that would be caused by hydrogen emission. And finally, the use of aqueous sodium hydroxide as a catalyst in place of the sodium metal that was used to catalyze the transesterification reaction described in U.S. patent application Ser. No. 160,786, filed June 16, 1980, is more efficient as less catalyst is required.

In accordance with the present invention, a mixed phosphoric acid ester composition is manufactured by heating about 2 moles of an alcohol characterized by a boiling point above about 170° C. and having the formula:

$$R_2CH_2CH_2OH$$

wherein $R_2$ is an alkyl radical with a catalytic amount (more than 1.5 moles percent based upon the alcohol) of an aqueous sodium hydroxide solution under vacuum to distill off the water present in the mixture and form sodium alkoxide in situ. The reaction mixture is then heated to about 100° C. under a blanket of nitrogen and about 1 mole of a triphenyl phosphate having the formula:

$$(R_1O)_3P=O$$

wherein $R_1$ is a phenyl radical, is added with agitation. The agitation is continued for about 1 hour while maintaining the reaction mixture at a temperature of about 100° C. under a nitrogen atmosphere. The by-product phenol and any residual aliphatic alcohols are then volatilized from the reaction mixture by applying vacuum and increasing the temperature from about 100° C. to about 140° C. The reaction mixture may be next filtered to remove any insoluble salts that are present and finally distilled under vacuum and at a temperature below the decomposition temperature of the mixed phosphoric acid ester composition formed to recover the desired product.

The alcohols that are useful in the process of the present invention are those having a boiling point above about 170° C. such as n-decanol and isodecanol. Particularly preferred is a mixture of isomeric $C_{10}$ alcohols that are substantially free of substitution on the alpha- and beta-carbon atoms that is a by-product of the petroleum industry. This alcohol may be purchased from the Exxon Chemical Company, Houston, Tex. having the following technical specifications:

| | |
|---|---|
| Acidity, as acetic acid (wt. percent) max | 0.001 |
| Appearance | Clear and Free of Suspended Matter |
| Carbonyl Number (mg KOH/g) max | 0.20 |
| Color (Pt-Co) max | 10.00 |
| Distillation (°C.) | |
| Initial min | 215.00 |
| Dry Point max | 223.00 |
| Purity (wt. percent) min | 99.00 |
| Specific Gravity (20/20° C.) max | 0.840 |
| Specific Gravity (20/20° C.) min | 0.835 |
| Water (wt. percent) max | 0.1 |

The aqueous sodium hydroxide solution that is employed to form sodium alkoxide in situ is conveniently added as a 50% aqueous solution. The water and any extraneous moisture that may be present in the triaryl phosphate and/or alcohol may conveniently be removed by azeotropic distillation. The actual amount of water that is present in the aqueous sodium hydroxide solution is not critical provided that sufficient water is present to obtain solubility of the sodium hydroxide in the alcohol used. More dilute solutions of sodium hydroxide than are required to obtain solubility should be avoided to minimize the energy required to remove the water from the reaction mixture. When isodecanol is employed as the alcohol, water may be removed at 100° C./4000 Pa (30 torr).

It has been noted that the amount of sodium hydroxide catalyst used to catalyze the transesterification reaction has an effect on the composition of the mixed ester and particularly the amount of triaryl phosphate that remains in the final product. Thus, when triphenyl phosphate is employed as the triaryl phosphate and isodecanol is used as the alcohol, the molar ratio of NaOH/isodecanol should be greater than 0.015 and no more than about 0.02 to maintain the amount of triphenyl phosphate in the final composition to less than 4%. It has been noted that increasing the amount of aqueous sodium hydroxide catalyst added to the reaction mixture decreases the weight percent of unreacted triphenyl phosphate but increases the weight percent of mixture of diisodecyl and isodecyl phenyl ethers. This effect of catalyst loading on ether formation and product composition when reacting triphenyl phosphate with isodecanol under the conditions described in Example I below is summarized in Table I.

The order of addition also has a pronounced effect upon the manufacturing process of the present invention. Thus, if aqueous sodium hydroxide is added to a mixture of a triaryl phosphate and an aliphatic alcohol, substantial quantities of sodium phosphate salts are formed as a by-product and the yield of the desired organic phosphate esters is diminished. The triphenyl phosphate should be added to the alcohol after all water has been removed.

The following examples are given by way of illustration of the instant invention and in no way limit the scope thereof. Parts and percentages are given by weight unless specified to the contrary.

EXAMPLE I

Preparation of Sodium Isodecylate

In a 12-liter round-bottom flask was placed 3900 g (24.7 moles) of isodecyl alcohol and to it was added 43.5 g of a 50% aqueous sodium hydroxide solution (2.2 mole percent of the alcohol charge). The flask was fitted with a mechanical stirrer, a thermometer, a distilling head condenser and receiver. Vacuum was applied to the side arm of the receiver to maintain a 4000 Pa (30 torr) pressure. The flask was then heated to 100° C. and maintained for 1 hour (with agitation) during which time water from the 50 % sodium hydroxide solution and some isodecyl alcohol were distilled overhead and collected. The vacuum pump was stopped and nitrogen was then introduced to the system to protect the alkoxide thus formed from oxidation.

Transesterification of Triphenyl Phosphate

Twelve moles (3900 g) of triphenyl phosphate was added to the contents of the above flask. The resulting mixture was maintained at 100° C. with stirring under a nitrogen atmosphere for 2.5 hours.

Removal of Lights

The excess of isodecyl alcohol and by-product phenol were removed by batch flash distillation under 133–266 Pa (1–2 torr) at a pot temperature of 100° C. First phenol then isodecyl alcohol were distilled overhead rapidly at 100° C. The distillation was continued as the pot temperature was gradually raised up to 140° C. at which temperature the lights-stripping step was terminated.

Filtration to Remove Salt

The stripped crude product from the preceding step was filtered through a coarse sintered glass filter under vacuum 2666–4000 Pa (20–30 torr) to remove any salt that may be present.

Wiped Film Distillation
First Pass To Remove Lights

The filtered product was transferred to the feed pot of a wiped film still. The skin temperature of the heating mantle was maintained at 200° C.–220° C. The pressure of the system was kept at 133 Pa (1 torr). The feed rate was controlled by a needle valve to maintain the underflow to overflow ratio at 10 to 1.

The underflow from the first pass through the still was charged to the feed pot and the skin temperature of the still column was maintained at 300° C.–330° C. It was noted that decomposition occurred if the temperature exceeded 330° C. The feed rate may be controlled by the valve to obtain a maximum yield of distillate. The underflow was primarily sodium diphenyl phosphate salt that was dissolved in the feed. The overflow mixed phosphate ester distillate weighed 3695 g (94.4% yield) and the underflow residue weighed 220 g (5.6% yield). Analysis of the product shows:

| | |
|---|---|
| Triphenyl Phosphate | 3.8% |
| Alkyl Diphenyl Phosphate | 77.3% |
| Diisodecyl Phenyl Phosphate | 18.9% |

When this experiment was repeated with a reduced amount of aqueous sodium hydroxide (20 g of 50% sodium hydroxide) or 1.0 mole percent based on the isodecyl alcohol charge, the analysis of the final product was:

| | |
|---|---|
| Triphenyl Phosphate | 10.9% |
| Isodecyl Diphenyl Phosphate | 78.2% |
| Diisodecyl Phenyl Phosphate | 10.9% |

EXAMPLE II

Transesterification with Isodecyl Alcohol

In a 2000 gallon steam jacketed kettle was placed 6144 pounds, 38.9 moles of isodecyl alcohol and 62 pounds of an aqueous 50% sodium hydroxide solution (0.2 mole percent based on the isodecyl alcohol). The kettle was fitted with a condenser, evacuated to 4000 Pa (30 torr) and heated to 100° C. with stirring. The water distilled over with alcohol as an azeotrope over a period of 1 hour. At that time, nitrogen was introduced into the kettle and 6155 pounds (18.9 moles) of melted triphenyl phosphate heated to 90° C. was introduced with stirring. Stirring was continued for an additional hour after introduction of the triphenyl phosphate while maintaining an atmosphere of nitrogen and maintaining the temperature at 100° C. The excess isodecanol and by-product phenol were then volatilized by increasing the temperature of the reaction product to 140° C. while reducing the pressure within the reaction kettle to 400–666 Pa (3–5 torr). During this preliminary distillation, 1490 pounds of phenol and 2058 pounds of isodecanol were recovered. The contents of the kettle were filtered at 60° C. and the filtrate was transferred to a wiped film still.

The first pass, 180° C.–200° C./133–400 Pa (1–3 torr) removes remaining phenol isodecyl alcohols and others. The underflow from the first distillation step was passed to the wiped film still a second time to rein the overhead 6160 pounds of mixed phosphoric acid ester composition, boiling at 224° C.–230° C./133–400 Pa (1–3 torr). The residue from the wiped film still weighed 400 pounds, which could be recycled to obtain additional product.

Gas chromatographic analyses of the distilled product indicated the following composition:

| Component | Weight Percent |
|---|---|
| Triphenyl Phosphate | 3.9% |
| Diphenyl Monoisodecyl Phosphate | 79.5% |
| Phenyl Diisodecyl Phosphate | 16.6% |

The effect of catalyst loading on the product distribution is shown in Table I.

TABLE I

Effect of Catalyst Loading on Ether Formation and Product Distribution

| Molar Ratio: Isodecanol/NaOH | 0.04 | 0.02 | 0.015 | 0.01 | 0.0075 | 0.0050 |
|---|---|---|---|---|---|---|
| Product Distribution | | | | | | |
| % Mixture of diisodecyl and isodecyl phenyl ethers | 4.7 | 2.0 | 1.2 | 0.9 | 0.7 | 0.2 |
| % Triphenylphosphate | 3.8 | 3.8 | 6.6 | 11.5 | 12.4 | 17.7 |
| % Isodecyl Diphenylphosphate | 71.0 | 77.5 | 79.6 | 78.2 | 78.9 | 74.1 |
| % Diisodecyl Phenylphosphate | 20.5 | 13.0 | 12.0 | 10.2 | 8.0 | 6.1 |

What is claimed is:

1. A process for the manufacture of a mixed phosphoric acid ester composition comprising less than about 4 weight percent of triphenyl phosphate having the formula:

$(R_1O)_3P=O$ from about 10 to about 20 weight percent of a phenyl dialkyl phosphate having the formula:

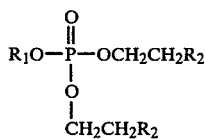

and from about 65 to 80 weight percent of an alkyl diphenyl phosphate having the formula:

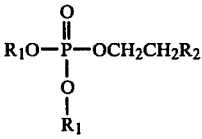

wherein $R_1$ is a phenyl radical and $R_2$ is an alkyl radical, which comprises:

(a) heating about 2 moles of an alcohol characterized by a boiling point above about 170° C. and having the formula:

$R_2CH_2CH_2OH$ with a catalytic amount of from greater than about 1.5 mole percent to about 2.0 mole percent based on the alcohol of an aqueous sodium hydroxide solution under vacuum to distill off the water present in the mixture and form a sodium alkoxide;

(b) adding about 1.0 mole of triphenyl phosphate of the formula:

$(R_1O)_3P=O$ to the reaction mixture under a nitrogen atmosphere and maintaining the temperature at about 100° C. with agitation for about an hour;

(c) heating the reaction mixture at 100° C. to 140° C. under vacuum to remove aromatic and aliphatic alcohols from the reaction mixture; and (d) distilling the filtrate in a wiped film still under vacuum and at a temperature below the decomposition temperature of said mixed phosphoric acid ester composition to obtain the desired product.

2. The process of claim 1 wherein the alcohol is n-decanol.

3. The process of claim 1 wherein the alcohol is isodecanol.

4. The process of claim 1 wherein the reaction mixture is filtered after removal of the aromatic and aliphatic alcohols and prior to distillation to remove any insoluble salts that may be present therein.

* * * * *